United States Patent [19]
Stolzy

[11] 3,986,388
[45] Oct. 19, 1976

[54] FLUID-PROPERTY DETECTION SYSTEM

[75] Inventor: Albert Donald Stolzy, Encino, Calif.

[73] Assignee: International Telephone and Telegraph Corporation, New York, N.Y.

[22] Filed: Sept. 5, 1975

[21] Appl. No.: 610,750

[52] U.S. Cl. .................................................. 73/59
[51] Int. Cl.² .......................................... G01N 11/16
[58] Field of Search ............... 73/54, 59, 67, 32 R

[56] References Cited

UNITED STATES PATENTS

| | | | |
|---|---|---|---|
| 2,607,217 | 8/1952 | Merten et al. ........................ | 73/54 |
| 3,181,348 | 5/1965 | Lewis ..................................... | 73/54 |
| 3,710,614 | 1/1973 | Opplinger ............................. | 73/54 |
| 3,712,117 | 1/1973 | Fitzgerald et al. ................... | 73/59 |

Primary Examiner—Richard C. Queisser
Assistant Examiner—Joseph W. Roskos
Attorney, Agent, or Firm—A. Donald Stolzy

[57] ABSTRACT

Apparatus for detecting the magnitude of a property of a fluid including a body mounted on a torsion spring that is oscillated by a feedback of alternately an in-phase and an out-of-phase signal from an amplifier having a gain adequate to sustain the oscillations. If the in-phase signal has a period directly proportional to $T_n$, the out-of-phase signal has a frequency directly proportional to $f_h$, and the out-of-phase period is directly proportional to $T_h$, then the magnitude of the property $p$ is determined by the digital computation of $$p = Kf_h(T_n - T_h) - B$$

where K and B are constants. The property $p$ may be any one of several properties including but not limited to viscosity.

11 Claims, 14 Drawing Figures

FLUID PROPERTY DETECTION SYSTEM

BACKGROUND OF THE INVENTION

This invention relates to the detection of a property of a fluid, and more particularly to viscosity or other fluid property magnitude detection.

In the past, prior art viscosimeters have had relatively poor accuracy.

SUMMARY OF THE INVENTION

In accordance with the system of the present invention, the abovedescribed and other disadvantages of the prior art are overcome by oscillating a body in a fluid with an amplified feedback impressed upon a driver with an in-phase and out-of-phase signal at alternate periods of time. It has then been found that if the oscillation frequency is directly proportional to $f_n$ and $f_h$ in the two sets of alternate periods, respectively, then the magnitude of a property of the fluid, including but not limited to viscosity, will be $$p = Kf_h (T_n - T_h) - B$$

where $T_h = 1/f_n$, and
K and B are constants.

In accordance with the invention, means are provided to compute p in accordance with the above equation.

The above-described and other advantages of the present invention will be better understood from the following detailed description when considered in connection with the accompanying drawings.

BRIEF DESCRIPTION OF THE DRAWINGS

In the drawings which are to be regarded as merely illustrative.

DESCRIPTION OF THE PREFERRED EMBODIMENTS

Figure 1:
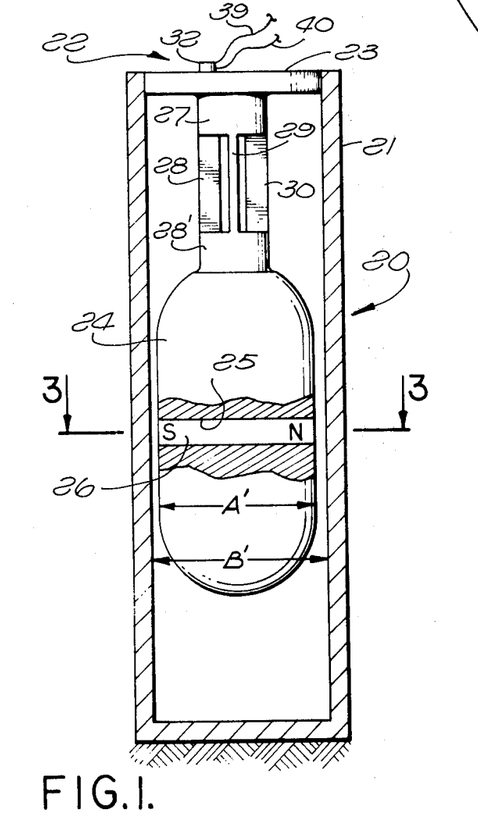
FIG. 1 is a vertical sectional view through a drag body assembly, partly in elevation.

In accordance with the present invention, a drag body assembly 20 may be employed which includes a cylindrical container 21 closed at its lower end, and a torsion spring assembly 22 having a disk 23 fixed inside of container 21 at the top thereof, all being shown in FIG. 1.

Disk 23 may be threaded into container 21, if desired. If so, a fluid sample may be inserted into container 21 by unscrewing disk 23 and injecting the sample into container 21 through the upper end thereof.

All of the structure shown inside container 21 and spaced from the internal cylindrical wall of container 21 may be integrally made from a single isotropic piece of metal or other material. However, there is one exception to this statement. A cylindrical portion or drag body 24 has a hole 25 therethrough in which a permanent magnet 26 is fixed. The location of permanent magnet 26 may be still better understood from the view of FIG. 3. A disk 27 is integral with disk 23. Four torsion strips 28, 29, 30 and 31 connect disk 27 to a disk 28' fixed relative to the torsion strips 28 to 31. Torsion strips 28 to 31 may also be observed in FIG. 2.

Figure 2:
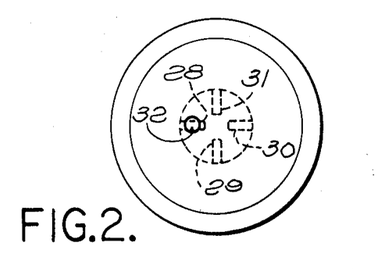
FIG. 2 is a top plan view of the assembly shown in FIG. 1.

In FIGS. 1 and 2, a piezoelectric crystal is illustrated at 32.

In FIG. 1, the diameter of drag body 24 is illustrated at A'. In the same FIG. 1, the inside diameter of container 21 is illustrated at B'. The inside diameter B' is greater than the outside diameter A' by an amount equal to 60 mils, if desired.

Figure 3:
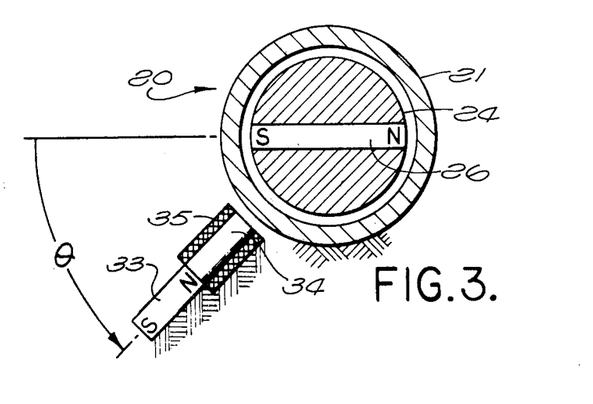
FIG. 3 is a tranverse sectional view taken on the line 3—3 of the assembly shown in FIG. 1.

As shown in FIG. 1, container 21 is fixed. As shown in FIG. 3, a permanent magnet 33, a ferromagnetic core 34 and a coil 35 around core 34 are fixed relative to container 21. The axis of permanent magnet 33, core 34 and coil 35 is perpendicular to the vertical axis of drag body 24 and makes an angle $\theta$ with the axis of permanent magnet 26 equal to, for example, 45°.

Figure 4:
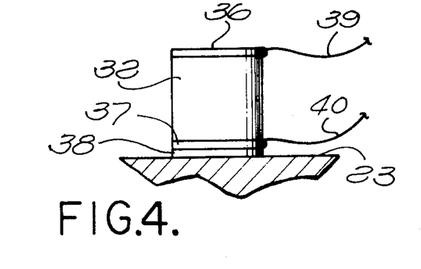
FIG. 4 is a broken away sectional view, partly in elevation, illustrating the mount of a piezoelectric crystal shown in FIGS. 1 and 2.

As shown in FIG. 4, crystal 32 may be mounted in any conventional way having an upper electrode 36, a lower electrode 37 and a bonding layer 38 bonding the lower electrode 37 to disk 23.

Upper electrode 36 has an electrical lead 39 connected therefrom. Lower electrode 37 has an electrical lead 40 connected therefrom. Both leads 39 and 40 are also shown in FIG. 1.

Figure 5:
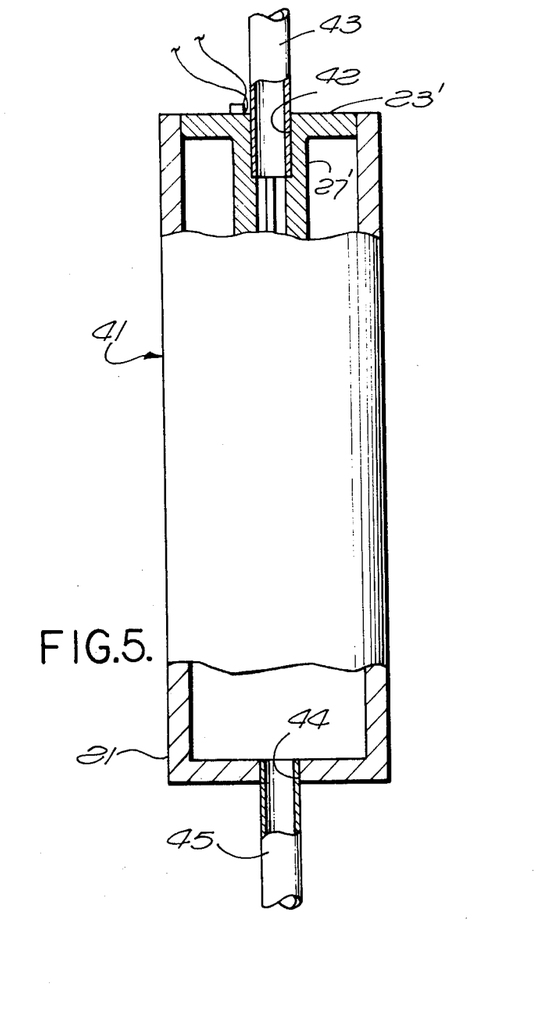
FIG. 5 is a vertical sectional view, partly in elevation, of an alternative embodiment of the present invention.

An alternative embodiment of the drag body assembly 20 is illustrated at 41 in FIG. 5. The drag body assembly 41 may be identical to drag body assembly 20 shown in FIG. 1 except that disk 23' corresponding to disk 23 in FIGS. 5 and 1, respectively, is provided with a hole 42 therethrough into which a tube 43 is sealed. If desired, the inside diameter of tube 43 may be approximately equal to or exactly equal to the spacing between each oppositely disposed pair of torsion strips 28 and 30, and 29 and 31. The hole 42 in disk 23' in FIG. 5 also extends completely through disk 27' corresponding to disk 27 in FIG. 1.

Drag body assembly 41 also is provided with a container 21' which may be identical to container 21 shown in FIG. 1, except that it is provided with a hole 44 therethrough into which a tube 45 is sealed. In accordance with the foregoing, as viewed in FIG. 5, fluid may be slowly circulated upwardly or downwardly in tubes 43 and 45.

Fluid can pass between the interior cylindrical surface of container 21 and drag body 24 in the space therebetween, the same having larger and smaller inside and outside diameters, respectively, at B' and A' shown in FIG. 1 and as described previously.

Figure 6:
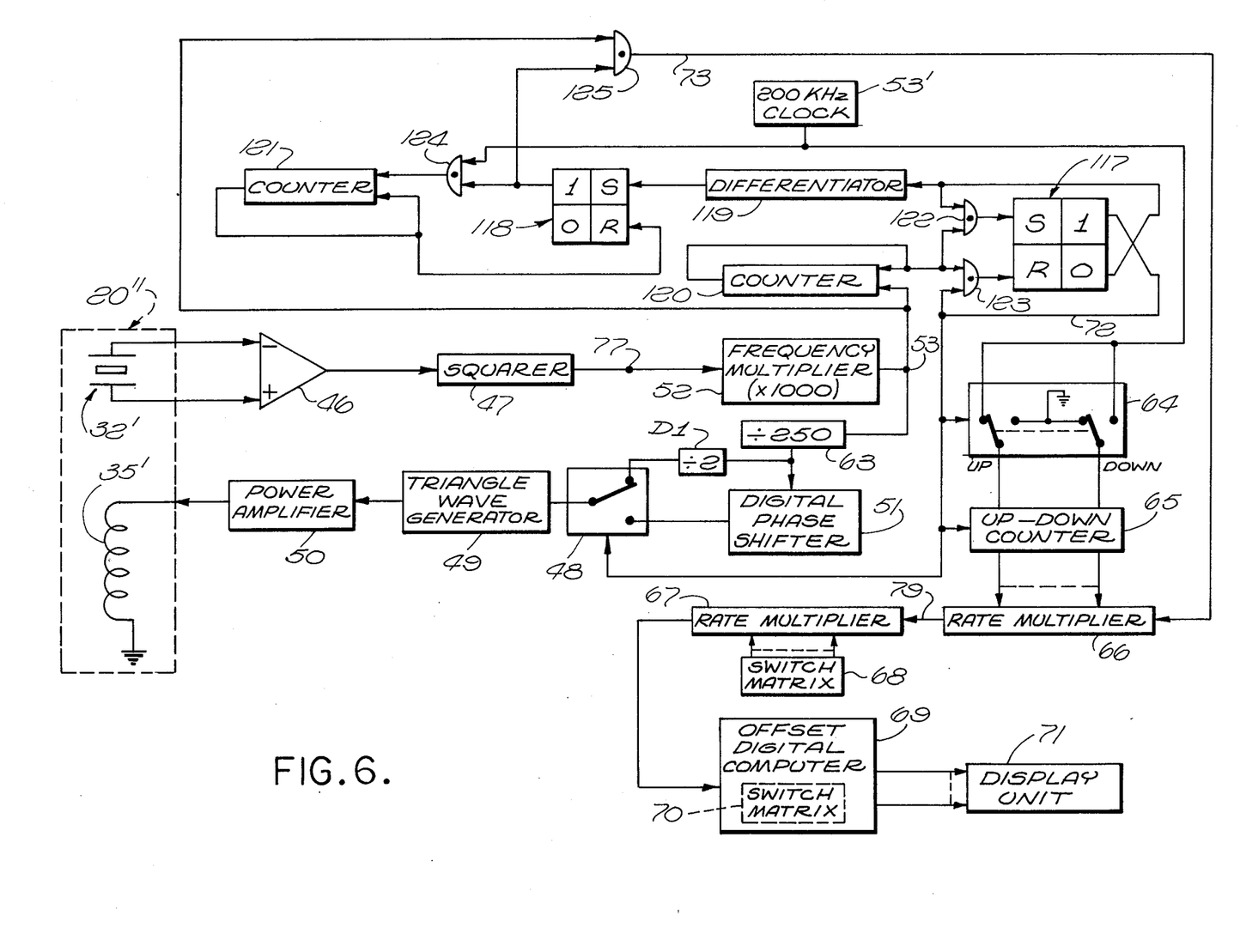
FIG. 6 is a block diagram of a system of the present invention employing a drag body assembly which may be of the type shown either in FIGS. 1, 2, 3 and 4, or in FIG. 5.

The system of the present invention is shown in FIG. 6 including a drag body assembly 20" which may be identical to assembly 20 or assembly 41 shown in FIGS. 1 and 5, respectively.

Assembly 20" has a piezoelectric crystal 32' corresponding, for example, to crystal 32 shown in FIG. 1, a coil 35' corresponding to coil 35 shown in FIG. 3. Assembly 20" with a differential amplifier 46, a squarer 47, a frequency multiplier 52, a divide-by-250 divider 63, either a divide-by-two divider D1 or a digital phase shifter 51, an electronic switch 48, a triangle wave generator 49, and a power amplifier 50 form a closed loop electromechanical oscillator wherein the gain is adequate to cause drag body 24, for example, in FIG. 3 to rotate back and forth or oscillate about its vertical axis, as viewed in FIG. 1. The peak-to-peak rotation is relatively small in amplitude (perhaps about one degree), and when the upper end of core 34 in FIG. 3 becomes positive, it provides additional attraction for the south pole of permanent magnet 26. Permanent magnet 26 provides permanent bias which may or may not allow the south pole of permanent magnet 26 to rise to or above the position in which it is shown in FIG. 3. When the upper end of core 34 becomes a south pole, both it and torsion spring assembly 22 tend to return permanent magnet 26 toward the position shown in FIG. 3, torsion spring assembly 22 resisting downward movement of the south pole of permanent magnet 26.

Coil 35' in FIG. 6 is supplied with an in-phase voltage when switch 48 is in the position shown. When switch 48 is in a position not shown, coil 35' is supplied with a signal which is, for example, 45 electrical degrees lagging the phase of output of amplifier 46.

The phase of the input to coil 35' when it lags the output of amplifier 46, in electrical degrees, is independent of frequency because of the use of digital phase shifter 51 shown in FIG. 6.

The said electromechanical oscillator is thus operated with a feedback without a phase shift during, for example, approximately one second, and with the said phase shift for approximately another second. This is done alternately so long as the system is in operation.

If desired, the output of a frequency multiplier 52 at a junction 53 may have a respective frequency and period $f_n$ and $T_n$ when the said electromechanical oscillator is operating without a phase shift. The output of frequency multiplier 52, when a phase shift exists in the oscillatory loop, may have a respective frequency and period $F_h$ and $T_h$.

Other components of the system of FIG. 6 include a 200 KHz clock 53', flip-flops 117 and 118, respectively, a differentiator 119, counters 120 and 121, respectively, AND gates 122, 123, 124 and 125, a divide-by-two hundred fifty divider 63, a double-pole, double-throw electronic switch 64, an up-down or reversible counter 65, a rate multiplier 66, a rate multiplier 67, a switch matrix 68, an offset digital computer 69 having a switch matrix 70, and a display unit 71.

Counter 120 is set to count perhaps 2.0 percent more than counter 121, both in the neighborhood of 200,000. Counter 120 thus alternately counts $f_n$ and $f_h$. The 1 output of flip-flop 117 thus controls 64, 65 and 48, the latter being in the $n$ position when the 1 output of flip-flop 117 is high. Counter 65 thus counts the clock up during $T_n$ and down during $T_h$. The output of counter 65 is then directly proportional to $(T_n - T_h)$. This difference is multiplied by a factor directly proportional to $f_h$ as follows.

Flip-flop 118 is set on the leading edge of the 1 output pulse of flip-flop 117 and reset by the reset pulse of counter 121. The 1 output of flip-flop 118 then opens AND gate 125 for a constant period of time. The number of pulses in each group at the output of AND gate 125 is then directly proportional to $f_h$ and each group number is impressed upon rate multiplier 66 and $f_n$ is thereby multiplied by the stored output in counter 65 [directly proportional to $(T_n - T_h)$]. Viscosity $p$ is thus indicated by display unit 71 because its input is directly proportional to $p$ where $p = Kf_h(T_n - T_h) - B$ and K and B are constants. The minimum value of $T_h$ should be greater than the period that the 1 output of flip-flop 118 is high.

Flip-flop 117 has a 1 output lead 72 which is high for about 1.0 second and low for about a second which follows, the same being a slow square wave with a mark-to-space ratio not equal to unity. Output lead 72 controls the position of switch 64, controls the updating of counter 65, and controls the alternate modes of oscillation of the said oscillatory loop by controlling the position of switch 48.

It is a nuance of the operation of the system of FIG. 6 that $f_h$ is larger than $f_n$. Conversely $T_n$ is larger than $T_h$ because $f_h = 1/T_h$ and $f_n = 1/T_n$. The system is therefore cycled by control of switch 64 to cause counter 65 to count the clock for $T_n$ in the up direction, and to count the clock thereafter for $T_h$ down when switch 64 is in the position not shown. In this way, the updated minimum count stored in counter 65 represents the difference $(T_n - T_h)$. This stored value is then multiplied by the pulses appearing at the output lead 73 of AND gate 125.

Squarer 47 is connected to a junction 77 which is also connected to the input of frequency multiplied 52. The frequency of the signal appearing at junction 77 when the output of frequency multiplier 52 is $f_n$ may be 200.000 hertz. The frequency of the signal appearing at junction 77 when $f_h$ exists may be 202.500 hertz.

The number stored in counter 65 is then multiplied by the number of pulses appearing on output lead 73 of AND gate 125 during the time that the 1 output of flip-flop 118 is high.

Switch matrix 68 in combination with rate multiplier 67 merely reduces the number of pulses at an output lead 79 of rate multiplier 66 so that the output of rate multiplier 67 is a number of pulses equal to $$Kf_h(T_n - T_h):$$

The factor K is set by adjustment of switch matrix 68. The factor B is subtracted by computer 69 by setting matrix 70. The output of computer 69 is impressed upon a display unit 71.

Frequency multiplier 52 may, for example, multiply the frequency of the square wave appearing at junction 77 by a factor of 1,000.

Triangle wave generator 49 may be replaced with a sine wave generator. It also may be replaced with a number of other components. The purpose of triangle wave generator 49 is to get a reasonably smooth fundamental current through coil 35'. The current which triangle wave generator 49 produces in coil 35' is illustrated at il in FIG. 13.

The combination of the structures illustrated in FIG. 6 is new. None of the individual components of the systems of FIG. 6 are per se new.

Divider 63 reduces the unnecessarily large frequency appearing at the output of frequency multiplier 52 to provide an input for digital phase shifter 51.

Figure 8:
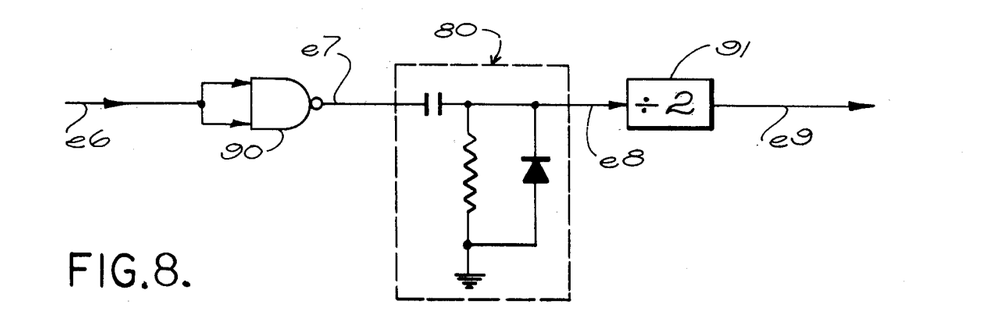
FIG. 8 is a block diagram of a digital phase shifter shown in FIG. 6.

All of the differentiators disclosed herein may be of the type illustrated at 80 shown in FIG. 8, the same being entirely conventional. Clock 53' may be entirely conventional. The same is true of divider 63.

The electronic switches 48 and 64 may be entirely conventional. The same is true of flip-flops 117 and 118, and counters 65, 120 and 121. The same is also true of AND gates 122, 123, 124 and 125 shown in FIG. 6. The same is true of differential amplifier 46, squarer 47 and power amplifier 50 shown in FIG. 6. The same is true of frequency multiplier 52, reversible counter 65, rate multiplier 66, rate multiplier 67, switch matrix 68, computer 69, switch matrix 70 and display unit 71.

Rate multipliers 66 and 67 may be identical to those disclosed in U.S. Pat. No. 3,878,374, or they may be otherwise conventional, as desired. The same is true of switch matrix 68, computer 69, switch matrix 70 and display unit 71. That is, all of the components 66, 67, 68, 69, 70 and 71 may be identical to the corresponding components disclosed in U.S. Pat. No. 3,878,374.

Counter 65 may be entirely conventional with or without updating. For example, see the numerous reversible counters in Handbook of Logic Circuits by John D. Lenk, (Reston Publishing Company, Inc., Reston, Virginia, copyright 1972).

OPERATION

In the operation of the system of FIG. 6, when the signal on the 1 output lead 72 of flip-flop 117 goes high, the switches 48 and 64 assume the positions shown. Counter 65 then counts up. This is true because switch 48, in the position shown, connects the output of divider D1 to triangle wave generator 49, and $f_n$ appears as the output of frequency multiplier 52, $f_h$ being larger than $f_n$ but $T_n$ being larger than $T_h$. Counter 65 then counts the clock up for the period $T_n$.

When the signal on output lead 72 goes low, the position of switch 64 is changed, and counter 65 counts the clock down for the period $T_h$. The prior stored period difference $(T_n - T_h)$ is, during the $T_h$ period, multiplied by a factor directly proportional to $f_h$ in rate multiplier 66. This is true because the width of the pulse at the 1 output of flip-flop 118 is constant and the number of pulses in each group within the said pulse width is directly proportional to $f_h$ because the high frequency input to AND gate 125 is, in fact, $f_h$. Thus, at the same time counter 65 is counting down, two registers therein, to be described, are employed to count down and to store at the same time. The stored difference between $T_n$ and $T_h$ is then multiplied by the pulses then appearing on the output lead 73.

For the operation of components 67, 68, 69, 70 and 71, see the said patent.

The system of FIG. 6 may be employed to indicate viscosity. Display unit 71 may so indicate.

The system of FIG. 6 is calibrated against a standard empirically. Calibration may be employed by using the method of least squares, or more easily, and perhaps less accurately, by reading display unit 71 for fluids of two different viscosities, measuring $f_h$ and $f_n$ at both of the viscosities, calculating $T_n$ and $T_h$, forming two simultaneous equations for the two different viscosities, and solving for the two unknowns K and B.

For the use of simultaneous equations and calibrating equipments empirically, see U.S. Pat. No. 3,677,067.

Figure 7:
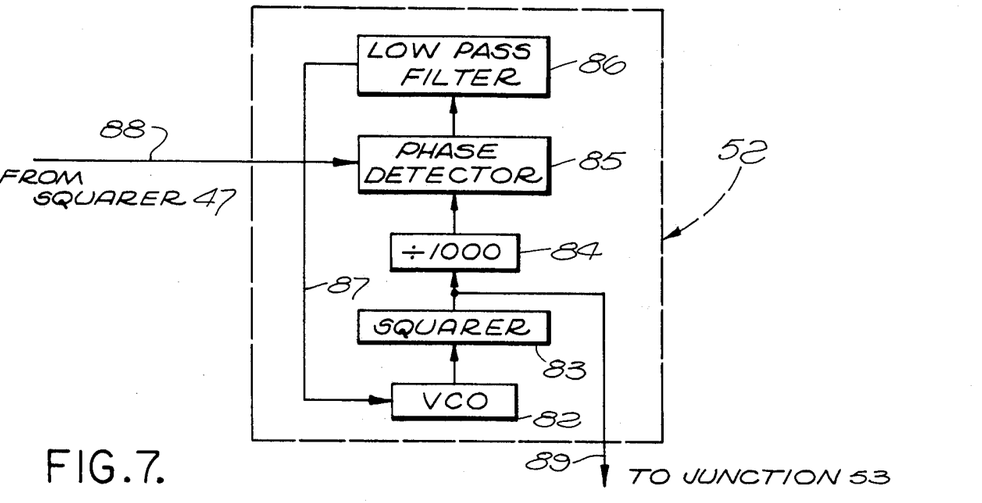
FIG. 7 is a block diagram of a frequency multiplier shown in FIG. 6.

Frequency multiplier 52 shown in FIG. 6 may be of the type shown in FIG. 7 or may be otherwise entirely conventional. Frequency multiplier 52 is provided with a voltage controlled oscillator (VCO) 82, a squarer 83, a divide-by-one thousand divider 84, a phase detector 85 and a low pass filter 86 connected in succession in that order. The output of low pass filter 86 is connected to the input of VCO 82 over a lead 87. The input to the frequency multiplier 52 is impressed upon phase detector 85 over an input 88.

Digital phase shifter 51 is shown in FIG. 8 including an inverter 90, differentiator 80 and a divide-two-two divider 91 connected in succession in that order.

Figure 9:
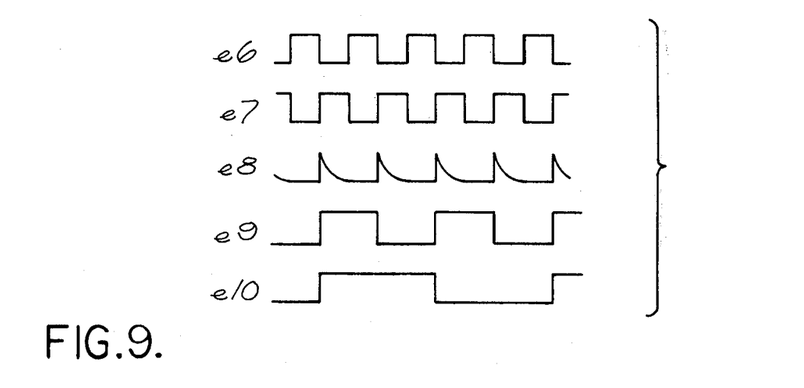
FIG. 9 is a graph of a group of waveforms characteristic of the operation of the digital phase shifter of FIG. 8.

The waveforms of FIG. 9 relate to FIG. 8. The waveforms of FIG. 9 are labeled in FIG. 8. The waveform e10 is the output of divide-by-two divider D2 in FIG. 12. The product of the amount divider 91 (FIG. 7) divides by and the amount divider 63 (FIG. 6) divides by must equal 500 because the frequency multiplier 52 in FIG. 6 multiplies by 1,000, and the frequency at the output of divider D2 (FIG. 12) must be the same frequency as the frequency of the waveform appearing at junction 77 regardless of the position of switch 48 shown in FIG. 6. The same is true of the divisor products of dividers D1 and 63 in FIG. 6. Note will be taken that the output e10 has been phase shifted 45 degrees in FIG. 9 because the trailing edge of input waveform e6 has been employed to trigger the leading edge of the waveform of e10.

Figure 10:
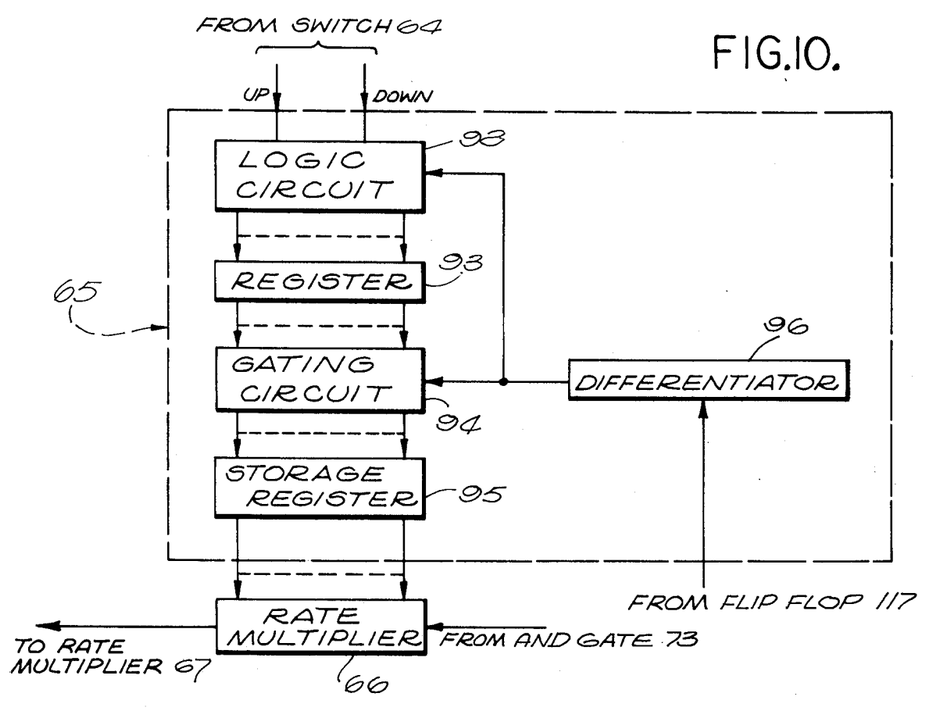
FIG. 10 is a block diagram of a reversible counter shown in FIG. 6 with a rate multiplier.

Counter 65 and rate multiplier 66 are again shown in FIG. 10. Counter 65 may or may not be conventional, as desired. Counter 65 employs a conventional logic circuit 92, a conventional counter-register 93 connected therefrom, a conventional gating circuit 94 connected from register 93, a conventional storage register 95 connected from gating circuit 94, storage register 95 being connected to rate multiplier 66.

Counter 65 is reset on the leading edge of the 1 output pulse of flip-flop 117 in FIG. 6 by a connection therefrom through a differentiator 96. The output of differentiator 96 is connected to logic circuit 92 and gating circuit 94. As is conventional, gating circuit 94 is employed to transfer the contents of counter-register 93 to storage register 95. The pulses appearing on the input lead to rate multiplier 66 from switch 57 are multiplied by the number stored in register 95, as is conventional.

The transfer of the contents of register 93 to register 95 through gating circuit 94 is demonstrated by a stage in each of the registers 93 and 95 corresponding to each other, and NAND gates in gating circuit 94 which accomplish the transfer function.

Figure 11:
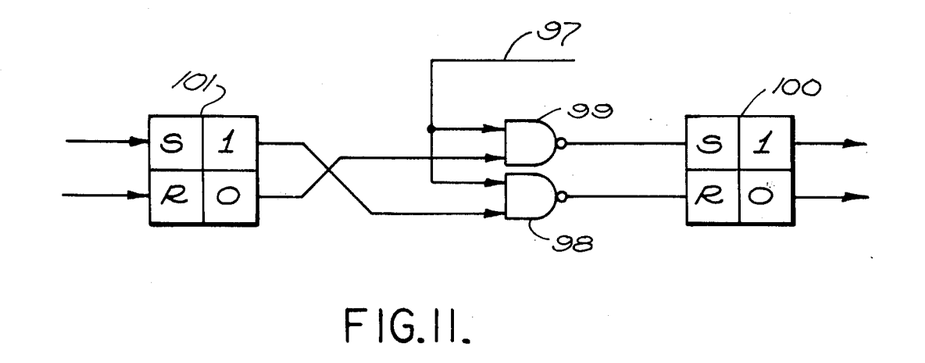
FIG. 11 is a block diagram illustrating a portion of two registers and a gating circuit shown in FIG. 10.

In FIG. 11, the output of differentiator 96 is impressed upon an input lead 97 which is connected to one input of each of two NAND gates 98 and 99 connected respectively to the set and reset inputs of a flip-flop 100. NAND gate 99 also receives an input from the "0" output of a flip-flop 101. NAND gate 98 also receives an input from the "1" output of flip-flop 101. Flip-flop 101 represents a stage in register 93 which corresponds with a stage in register 95 including flip-flop 100.

Figure 12:
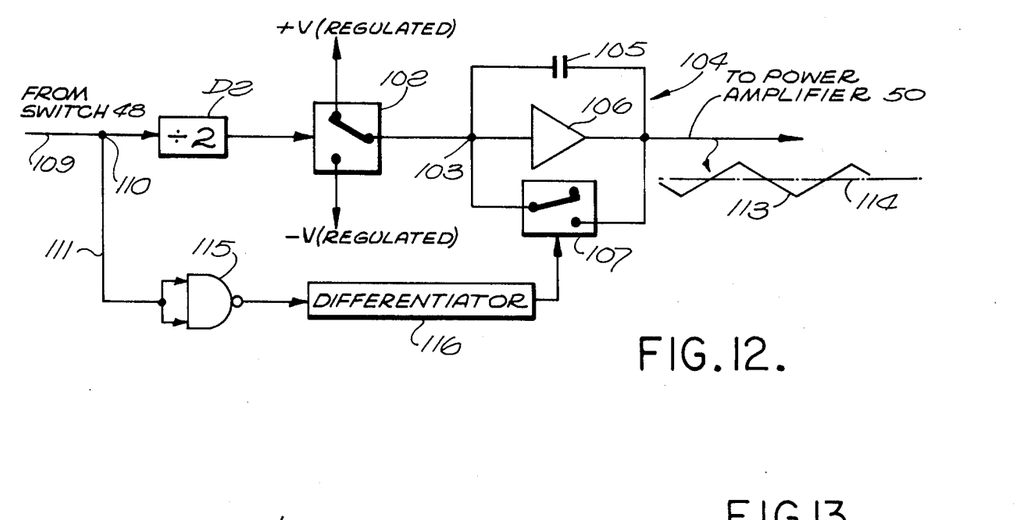
FIG. 12 is a block diagram of a triangle wave generator shown in FIG. 6.

Triangle wave generator 49 is shown in FIG. 12 including an electronic switch 102 operated by the output (pole) of switch 48 shown in FIG. 6.

In FIG. 12, a square wave having a regulated positive and negative value, the absolute value of each being regulated to an identical value, if possible, is impressed upon an input junction 103 of a conventional integrator 104 having a feedback capacitor 105, an amplifier 106 and an electronic reset switch 107 operated by the output of a differentiator 116. Triangle wave generator 49 has an input lead 109 connected from the pole of switch 48 shown in FIG. 6. In FIG. 12, input lead 109, as stated previously, is connected to control the position of switch 102, but also forms a junction 110 with a lead 111.

Divider D2, inverter 115 and differentiator 116 are employed to zero integrator 104 and thereby to prevent drift. As shown, integrator 104 is zeroed each time the triangular wave output 113 thereof passes through zero volts at 114. Zeroing may be performed less often, if desired. Zeroing may be employed once per cycle of waveform 113, or less often. Inverter 115 and a differentiator 116 are connected from lead 111 to reset switch 107.

In accordance with the foregoing, the leading and trailing edges of each pulse received over input lead 109 is detected by differentiator 116 and pulses at those points in time are employed to close switch 107 at the trailing edges of the pulses appearing on input lead 109.

Figure 13:
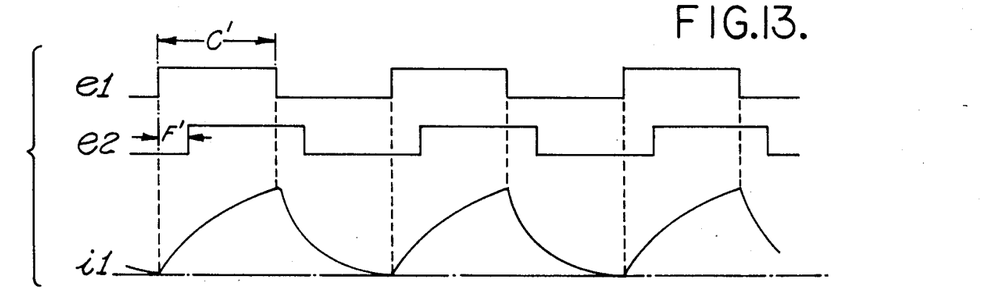
FIGS. 13 and 14 are graphs of groups of waveforms characteristic of the operation of the system of the invention shown in FIG. 6.

In FIG. 13, e1 represents the square wave appearing at the output of switch 48 in the position shown in FIG. 6. The waveform e1 is also impressed upon the input lead 109 of triangle wave generator 49 shown in FIGS. 6 and 12, respectively. The same waveform when switch 48 is in the other of its positions in FIG. 6 appears at e2. Although, as shown, the waveforms may (e1 and e2) have no time correspondence, they are shown in time correspondence to illustrate that the waveform e2 which always appears at junction 77 in FIG. 6 is always 45 degrees out of phase with the waveform e1. Note will be taken that the waveform e2 lags wavefrom e1 by 45 degrees in FIG. 13.

As stated previously, the output of switch 48 in its two different positions have no time correspondence because the switch 48 in FIG. 6 is in only one position at a time, obviously. The phases of the two different output signals of switch 48 on the pole thereof as shown in FIG. 6 therefore are unrelated. Although the frequency of the square wave appearing at junction 77 in FIG. 6 is always nearly the same, it is in fact the two different frequencies thereat by which viscosity is calculated. The properties of a fluid other than viscosity may also be calculated in the same way as disclosed in FIG. 6.

The time dimension C' shown in waveform e1 may be substantially equal to the time width of each pulse in waveform e2 in FIG. 13, although, as stated previously, there is a finite difference which is important, and which is employed to compute viscosity, et cetera. The pulse width C' may be, for example, 5 milliseconds or so.

When switch 48 in FIG. 6 is in the position not shown, e1 may represent the waveform appearing at junction 77, and e2 may represent the waveform at the output of divider D2 in FIG. 12. The dimension F', in comparing waveforms e1 and e2 in FIG. 13, may be equal to C' divided by 4.

When switch 48 is in the position shown in FIG. 6, the waveform appearing at junction 77 and the waveform at the output of divider D2 in FIG. 12 may be identical to, in phase, and represented by e1.

The current in coil 35' may be similar regardless of the position of switch 48. It may have a shape as indicated at i1 shown in FIG. 13, for example, when switch 48 is in a position shown.

Figure 14:
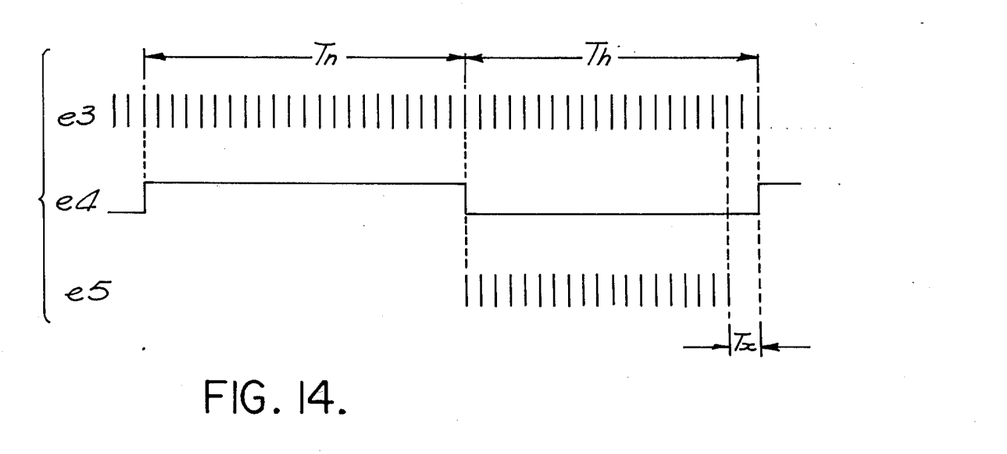

In FIG. 14 e3 is the pulse output of clock 53'. Waveform e4 is the 1 output of flip-flop 117.

The pulses e3 during period $T_n$ in FIG. 14 represent the clock pulse count between successive set and reset pulses to flip-flop 117. After counter 65 has counted the clock up during period $T_n$ corresponding to the illustrated period $T_n$ but prior thereto, and counter 65 has counted the clock down during a period prior to but corresponding to period $T_h$, the difference count contained in register 93 of FIG. 10 is then transferred to register 95 at the beginning of period $T_n$ shown in FIG. 14. Counter 65 then counts the clock up again for the $T_n$ period shown in FIG. 14 and, on the count down during illustrated period $T_h$ shown in FIG. 14, at the same time multiplication is provided by rate multiplier 66 as will be explained.

The pulses at e5 in FIG. 14 represent the output pulses of AND gate 125 shown in FIG. 6 which are passed to the input of rate multiplier 66 in FIG. 6. The input pulses to rate multiplier 66 shown in FIG. 6 come in groups because AND gate 125 does not pass $f_h$ pulse except over a constant period determined by the length of counter 121, which may be slightly less than the maximum expected period $T_h$ [the difference is exaggerated at $T_x$ for clarity in FIG. 14 — the difference ($T_n - T_h$) is also exaggerated in FIG. 14 for the same reason]. The period during which one pulse group of the pulses e5 in FIG. 14 are produced depends upon the size of counter 121 shown in FIG. 6.

The word switch is hereby defined for use herein and for use in the claims to mean any kind of switch, but preferably an electronic or electrical switch. Further, the word switch is hereby defined herein for use herein and for use in the claims to mean preferably an electronic switch.

The flow through container 21' shown in FIG. 5, and as described hereinbefore, is preferably moderate, slow, or very slow.

Because the energization of coil 35 shown in FIG. 3 causes the oscillatory rotation of drag body 24, it will be appreciated that containers 21 and 21' and perhaps all of the structures therein are preferably nonmagnetic except for permanent magnet 26 shown in FIGS. 1 and 3.

The equation set forth hereinbefore may be employed to measure density if viscosity is maintained substantially or exactly constant. Similarly, in order to display viscosity at display unit 71 shown in FIG. 6, it can be important to maintain the fluid in container 21, for example, shown in FIG. 1 at a constant temperature so as to maintain the density of the fluid therein constant. Viscosity may also be maintained constant if density is to be metered or the like.

Torsion spring assembly 22 shown in FIG. 1 may be provided with any conventional torsion spring, torque tube or torque rod, if desired.

Also, as stated previously, one or more magnitudes of one or more respective fluid properties may appear at the output of computer 69 in FIG. 6 and be used in combination with any one or more components for the computation of other variables in a larger system. In addition, the system of FIG. 6 may be employed to indicate the magnitude of a fluid property at display unit 71, or display unit 71 may be replaced by a process controller or otherwise. This is true regardless of what magnitude of what fluid property is represented by the output of computer 69 in FIG. 6.

The word fluid as used herein and for use in the claims is hereby defined to be a liquid unless the invention is useful in the determination of a fluid property of one or more or all gases.

The phrases "AND gate" and "NAND gate" as used herein and in the claims each mean either an AND gate or a NAND gate each with or without an inverter.

It is important to note that digital phase shifter 51 shown in FIG. 6 is a phase shifter which shifts the phase of the square wave appearing at junction 77 shown in FIG. 6 independent of the frequency of the square wave appearing at the said junction 77.

The maximum rotary movement of drag body 24 in FIGS. 1 and 3 may or may not be 1.0°.

This invention is similar in some respects to copending application Ser. No. 602,384 filed Aug. 5, 1975, by G. L. SCHLATTER and C. E. MILLER for FLUID PROPERTY DETECTION SYSTEM.

What is claimed is:

1. In a system for producing an output directly proportional to the magnitude of a property of a fluid, the combination comprising: an electromechanical oscillator including a body movably mounted in a manner to be at least partially immersed in a fluid, sensor means to produce a first periodic signal responsive to oscillation of said body, first means connected from said sensor means to receive said first periodic signal, electrical drive means mounted to oscillate said body, said first means including an amplifier and supplying second and third periodic signals having first and second frequencies, respectively, substantially equal to those of said first periodic signal at different corresponding times, said first means supplying said second and third periodic signals to said electrical drive means to cause the same to oscillate said body and to form a closed loop, said first means producing signals of frequencies $f_n$ and $f_h$ having respective periods $T_n$ and $T_h$, the gain of said amplifier being adequate to cause said loop to have sustained oscillations at one of said first and second frequencies directly proportional to said frequencies $f_n$ and $f_h$, said first means including a phase shifter connected to receive a signal of said first periodic frequency, said first means applying said second and third period signals to said electrical drive means alternately on a time shared basis, said second periodic signal, when applied, being in phase with said first periodic signal, said third periodic signal, when applied, being out of phase with said first periodic signal; second means connected from said sensor means for counting cycles at a rate directly proportional to $f_h$ for a period of time directly proportional to $(T_n - T_h)$; and third means connected from said second means for producing an output $p$ in accordance with the equation $$p = Kf_h (T_n - T_h) - B$$

where K and B are constants.

2. The invention as defined in claim 1, wherein $p$ is viscosity.

3. The invention as defined in claim 2, wherein a hollow cylinder is provided, said body having an external cylindrical surface mounted in a substantially fixed axial but rotatable angular position concentrically within said hollow cylinder, said hollow cylinder having an internal cylindrical wall, said hollow cylinder containing the fluid, said body cylindrical surface being positioned contiguous to said internal cylindrical wall of said cylinder.

4. The invention as defined in claim 3, wherein said body is suspended in said fixed axial position from said cylinder by a torsion spring, said drive means being elctromagnetic.

5. The invention as defined in claim 4, wherein said phase shifter includes a digital phase shifter, a clock, a single-pole, double-throw (SPDT) switch effectively having first and second contacts, said first contact being connected to receive said second and third periodic signals, respectively, said first means including a frequency multiplier connected to receive a signal directly proportional to said first periodic signal, said digital phase shifter being connectible from said frequency multiplier to said second contact.

6. The invention as defined in claim 5, wherein a reversible counter is provided, gating means connected from said frequency multiplier and from said clock, effectively a double-pole, double-throw (DPDT) switch, said DPDT switch being connected from the output of said gating means to said reversible counter to cause the output of said reversible counter to be directly proportional to the difference $(T_n - T_h)$, said gating means having one output to operate said SPDT and DPDT switches in synchronism, first and second rate multipliers connected in that order, a reset counter for clock pulses, gate means connected from said reset counter and connected from the output of said frequency multiplier to pass $f_h$ pulses over a constant period of time to the input of said first rate multiplier, said first rate multiplier being connected from said reversible counter, a first switch matrix connected to said second rate multiplier to set said constant K, an offset digital computer including a second switch matrix to set said constant B, and utilization means, said offset digital computer and said utilization means being connected in succession in that order from said second rate multiplier.

7. The invention as defined in claim 2, wherein said phase shifter includes a digital phase shifter, a clock, a single-pole, double-throw (SPDT) switch effectively having first and second contacts, said first contact being connected to receive said second and third periodic signals, respectively, said first means including a frequency multiplier connected to receive a signal directly proportional to said first periodic signal, said digital phase shifter being connectible from said frequency multiplier to said second contact.

8. The invention as defined in claim 1, wherein said phase shifter includes a digital phase shifter, a clock, a single-pole, double-throw (SPDT) switch effectively having first and second contacts, said first contact being connected to receive said second and third periodic signals, respectively, said first means including a frequency multiplier connected to receive a signal directly proportional to said first periodic signal, said digital phase shifter being connectible from said frequency multiplier to said second contact.

9. The invention as defined in claim 8, wherein a reversible counter is provided, gating means connected from said frequency multiplier and from said clock, effectively a double-pole, double-throw (DPDT)

switch, said DPDT switch being connected from the output of said gating means to said reversible counter to cause the output of said reversible counter to be directly proportional to the difference ($T_n - T_h$), said gating means having one output to operate said SPDT and DPDT switches in synchronism, first and second rate multipliers connected in that order, a reset counter for clock pulses, gate means connected from said reset counter and connected from the output of said frequency multiplier to pass $f_h$ pulses over a constant period of time to the input of said first rate multiplier, said first rate multiplier being connected from said reversible counter, a first switch matrix connected to said second rate multiplier to set said constant K, an offset digital computer including a second switch matrix to set said constant B, and utilization means, said offset digital computer and said utilization means being connected in succession in that order from said second rate multiplier.

10. The invention as defined in claim 9, wherein $p$ is viscosity.

11. The invention as defined in claim 10, wherein a hollow cylinder is provided, said body having an external cylindrical surface mounted in a substantially fixed axial but rotatable angular position concentrically within said hollow cylinder, said hollow cylinder having an internal cylindrical wall, said hollow cylinder containing the fluid, said body cylindrical surface being positioned contiguous to said internal cylindrical wall of said cylinder.

* * * * *